United States Patent [19]

Ichihashi et al.

[11] Patent Number: 4,877,321
[45] Date of Patent: Oct. 31, 1989

[54] SLIT LAMP MICROSCOPE

[75] Inventors: Tadashi Ichihashi; Masunori Kawamura, both of Tokyo, Japan

[73] Assignee: Kowa Company Ltd., Japan

[21] Appl. No.: 311,424

[22] Filed: Feb. 14, 1989

Related U.S. Application Data

[63] Continuation of Ser. No. 059,735, Jun. 8, 1987, abandoned.

[30] Foreign Application Priority Data

Jun. 6, 1986 [JP] Japan .................................. 61-130060

[51] Int. Cl.[4] .............................................. A61B 3/10
[52] U.S. Cl. ...................................... 351/214; 351/221
[58] Field of Search ............... 351/205, 206, 217, 214, 351/221; 128/303.1

[56] References Cited

U.S. PATENT DOCUMENTS 3,703,176 11/1972 Vassiliadis et al. ................ 351/221
4,213,678 7/1980 Pomerantzeff et al. ............ 351/221
4,741,612 5/1988 Birngruber .......................... 351/221

Primary Examiner—Rodney B. Bovernick
Assistant Examiner—P. M. Dzierzynski
Attorney, Agent, or Firm—Bruce L. Adams; Van C. Wilks

[57] ABSTRACT

A slit lamp microscope for use in observing the cornea, crystalline lens and other tissues of an eye includes a scanning device for scanning the laser beam vertically and horizontally within a selected area of the eye to be examined to form thereon a slit image which illuminates the selected area. A regulating device is provided for regulating the intensity of the laser beam to a predetermined level depending upon the amount of light reflected from the eye. The scanning device is controlled to change its scanning area to make the selected area variable to thereby provide a slit image which is changeable in size.

7 Claims, 2 Drawing Sheets

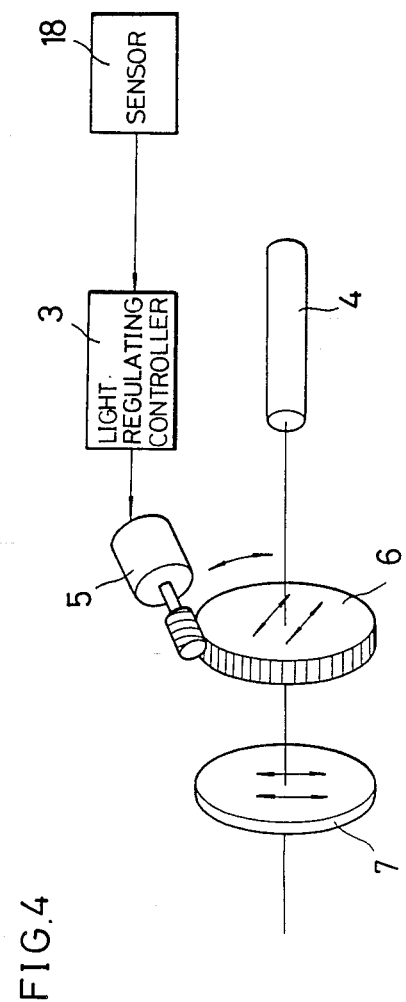
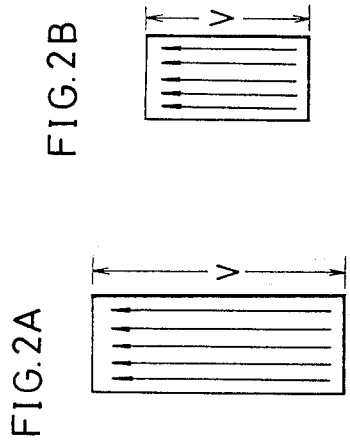

SLIT LAMP MICROSCOPE

This is a continuation of application Ser. No. 059,735, filed June 8, 1987 now abandoned.

BACKGROUND OF THE INVENTION

1. Field of the Invention

This invention relates to a slit lamp microscope and more particularly to a slit lamp microscope adapted for use in examination and diagnosis with respect to such tissues of the eye as the cornea and crystalline lens.

2. Description of the Prior Art

In the conventional slit lamp microscope, the white light from a light source such as a halogen lamp is passed through a slit formed between the opposing edges of two shield plates, the beam obtained in this way is directed onto an eye to be examined and the state of the cornea, crystal line lens etc. of the eye are observed using the light scattered by these eye tissues.

Because of its use of a halogen lamp or the like, however, the conventional slit lamp microscope has low illuminating light intensity and, as a result, it has not been possible with the microscope to observe slight cloudiness, turbidity and the like. Moreover, since the width of the slit is varied by adjusting the gap between the two shield plates, the quantity of light illuminating the eye under examination grows smaller as the width of the gap is narrowed. It has thus been impossible to reduce the size of the observation region beyond a certain limit.

SUMMARY OF THE INVENTION

One object of the invention is to provide a slit lamp microscope in which the intensity of the illuminating light is high and the ratio between the length and width of the illuminating light cross-section can be accurately adjusted over a wide range.

Another object of the invention is to provide a slit lamp microscope in which the quantity of illuminating light is not changed when the width of the light from the slit is narrowed.

The slit lamp microscope according to the present invention is used to observe the cornea, crystalline lens and other tissues of the eye. It comprises a laser source for producing a laser beam; a projector for projecting the laser beam onto the eye to be examined; scanning means for scanning the laser beam vertically and horizontally within a selected area of the eye to be examined to form thereon a slit image which illuminates the selected area; optical means for receiving light scattered by the selected area of the eye to be examined and/or photographing an image of the eye; and light regulating means for regulating the intensity of the laser beam to a predetermined level depending upon the quantity of light received by the optical means.

In the preferred embodiment of the invention, the scanning area defined by the scanning means is made variable to provide a slit image or pattern which is variable in size. The light regulating means includes a pair of linear polarizers through which the laser beam passes. One of the linear polarizers is caused to be rotated relative to the other to regulate the intensity of the laser beam depending upon the quantity of light received by the optical means.

With the aforesaid arrangement according to the present invention, by scanning a laser beam of high light intensity in the vertical and horizontal directions, it becomes possible to freely adjust the ratio between the length and width of the illuminating light cross-section. In particular, if the horizontal scanning width is reduced to the width of a single laser beam, it becomes possible to observe a cross-section of the cornea, crystalline lens or the like using an extremely narrow slit beam.

Moreover, the invention makes it possible to maintain the quantity of received light at a constant value regardless of changes in the dimensions of the slit beam.

Further, since the intensity of the laser light is high, it becomes possible to reliably conduct examination and diagnosis even with respect to slight disorders of the cornea, crystalline lens and the like, which facilitates early detection of diseases of the eye.

BRIEF DESCRIPTION OF THE DRAWINGS

The objects and features of the present invention will become more apparent from a consideration of the following description taken in conjunction with the accompanying drawings in which:

FIGS. 2A and 2B are explanatory views indicating the manner in which scanning of the laser beam in the vertical direction is conducted;

FIGS. 3A and 3B are explanatory views indicating the manner in which scanning of the laser beam in the horizontal direction is conducted; and FIG. 4 is an explanatory view of the light quantity adjustment system.

DETAILED DESCRIPTION OF THE INVENTION

Figure 1:
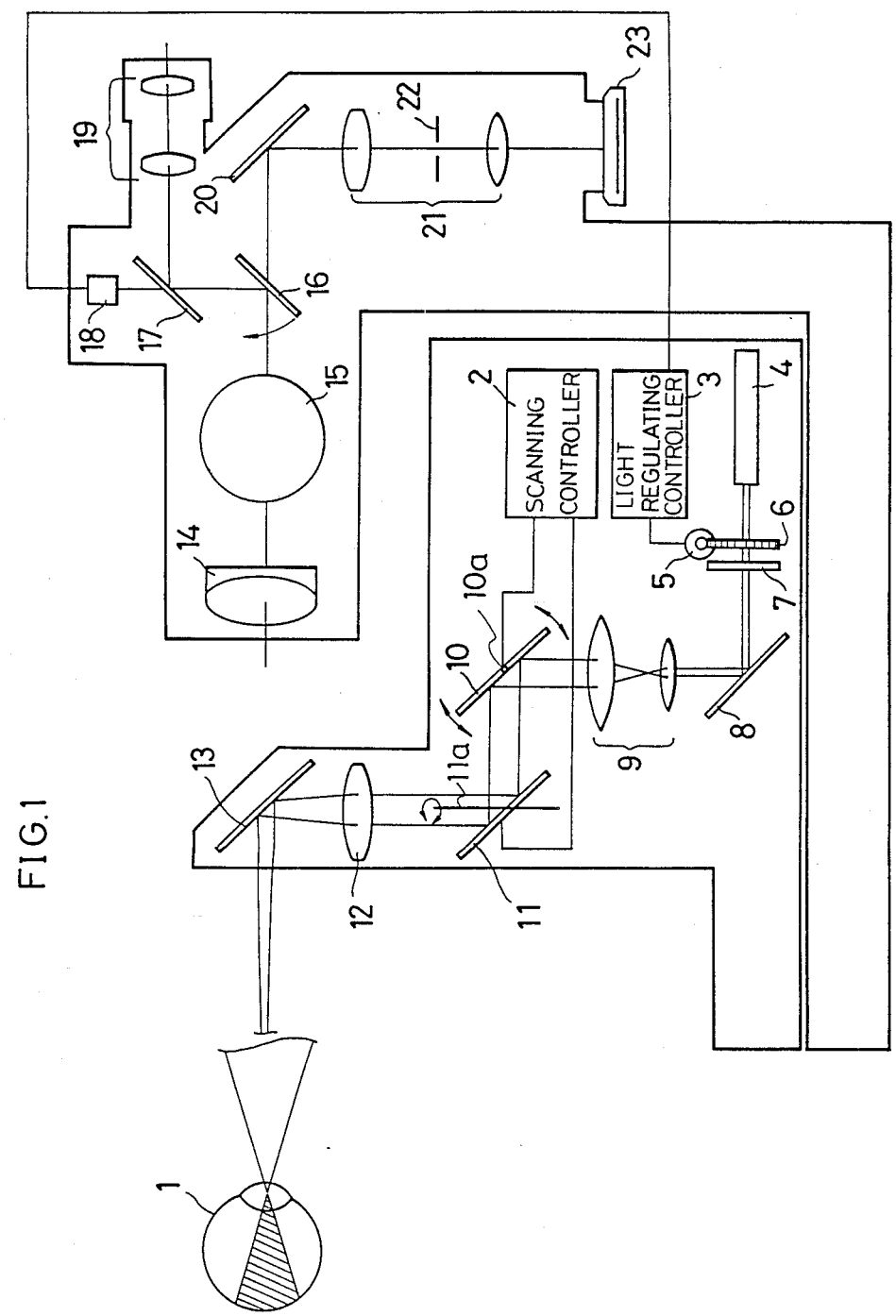
FIG. 1 is a schematic diagram of the slit lamp microscope according to the present invention.

The invention will now be described with reference to the attached drawings.

Referring to FIG. 1, for illuminating an eye 1 to be examined, the slit lamp microscope has an illuminating optical system consisting of a laser source 4, linear polarizers 6 and 7, a reflecting mirror 8, a beam expander 9, a reflecting mirror 10 for vertical scanning, a reflecting mirror 11 for horizontal scanning, a projection lens 12 and a reflecting mirror 13.

The slit lamp microscope further has an optical system for visual and photographic observation of a cross-sectional image produced from the light scattered by the eye 1. More specifically, light scattered from the eye 1 and traveling along a different optical path from that of the illuminating light enters an objective lens 14, passes through a variable power optical system 15 and impinges on a swingable reflecting mirror 16. In the case of visual observation, the swingable mirror 16 reflects the light beam onto a beam splitter 17, from which a part of the beam is reflected into an eyepiece 19 for observation by the operator. The remainder of the beam is transmitted through the beam splitter 17 to a light quantity sensor 18 which detects the quantity of light and sends a corresponding signal to a light regulating controller 3 to be described later. In the case of photographic observation, the swingable mirror 16 swings upward, allowing the light beam from the variable power optical system 15 to be reflected by a reflecting mirror 20, to pass through photographic lens 21, 22 and a stop 22, and thereby to be projected onto the surface of a photographic film 23.

For producing the slit beam, the slit lamp microscope is provided with a scanning means for scanning the laser beam in the horizontal and vertical directions along a locus. This means is constituted by the reflecting mirror 10 for the vertical scanning, the reflecting mirror 11 for the horizontal scanning and a scanning controller 2. The scanning controller 2 is equipped with a drive mechanism for synchronously driving the reflecting mirror 10 to oscillate about a shaft 10a (extending perpendicularly to the drawing sheet) and synchronously driving the reflecting mirror 11 to oscillate about a shaft 11a.

As shown in FIGS. 2A and 2B, the amount of oscillation of the reflecting mirror 10 can be controlled to vary the scanning range V in the vertical direction, while, as shown in FIGS. 3A and 3B, the amount of oscillation of the reflecting mirror 11 can be controlled to vary the scanning range H in the horizontal direction. The reflecting mirrors 10 and 11 are independently controlled by the scanning controller 2 with respect to scanning velocity and scanning range.

The maximum quantity of the laser beam light is restricted so as not to exceed the safety standards and the adjustment is carried out to attenuate the light quantity from this maximum quantity by means of the light regulating controller 3, the pair of linear polarizers 6 and 7 and the light quantity sensor 18. As shown in FIG. 4, the light quantity sensor 18 detects the light quantity and sends an electrical signal representing the detected light quantity to the light regulating controller 3. A motor 5 is driven by the light regulating controller 3 to rotate the linear polarizer 6 in such manner than when the light quantity is too large, the linear polarizer 6 is rotated with respect to the linear polarizer 7 so as to bring the angle of intersection between the polarization directions of the linear polarizers 6 and 7 (see arrows) closer to 90 degrees, in this way increasing the amount of attenuation and reducing the light quantity. On the contrary, when the quantity of light is insufficient, the linear polarizer is rotated to bring the polarization directions of the linear polarizers 6 and 7 closer to the alignment, in this way decreasing the amount of attenuation and increasing the light quantity. While the adjustment of the light quantity has been described here as being carried out automatically, it is alternatively possible to carry out the adjustment by manually rotating the linear polarizer 6.

Further, the linear polarizers 6 and 7 can be replaced by a continuously variable ND filter of rotationally adjustable type.

The operation of the slit lamp microscope of the aforesaid arrangement will now be explained.

The laser beam produced by the laser 4 has its light quantity adjusted by the linear polarizers 6 and 7 and then is passed through the beam expander 9 to have its beam diameter enlarged. The loser bam is then scanningly deflected by the reflecting mirrors 10 and 11 so as to produce an appropriate slit beam, and the scanningly deflected beam (slit beam) then proceeds through the projection lens 12 to the reflecting mirror 13 from which it is reflected to illuminate the eye 1.

Light scattered from within the eye 1 enters the optical system for visual and photographic observation. The incoming scattered light is first converged by the objective lens 14 and then enters the variable power optical system 15 where the observation magnfication is determined. Next, in the case of visual observation, the scattered light is reflected in the direction of the visual observation optical system (in the direction of beam splitter 17) by the swingable mirror 16, and in the case of photographic observation, the scattered light is passed in the direction of the photographic optical system (in the direction of reflecting mirror 20). During visual observation, the scattered light reflected by the swingable mirror 16 is divided into two beams by the beam splitter 17, one of which advances to the eyepiece 19 and the other of which advances to the light quantity sensor 18. As was mentioned earlier, the light quantity sensor 18 sends a signal representing the light quantity to the light regulating controller 3 which then adjusts the quantity of light based on the signal. Alternatively, however, it is possible for the operator examining the cornea, crystalline lens or the like through the eyepiece 19 to control the quantity of light by manually adjusting the linear polarizer 6.

During photographic observation, the scattered light passed to the photographic optical system is reflected toward the photographic lenses 21 by the reflecting mirror 20, whereby the film 23 is exposed to a projected cross-sectional image of the cornea, crystalline lens or the like.

In the illumination of the eye with the slit beam, the vertical scanning range V and the horizontal scanning range H can be appropriately varied as desribed earlier by the manner in which the scanning controller 2 drives the reflecting mirrors 10 and 11 to designate an area to be observed. The area of the slit can thus be varied by adjusting the scanning ranges, and if the light quantity of the slit beam should be changed, it is automatically readjusted by the light regulating controller 3 to maintain the light quantity constant.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. A slit lamp microscope for observing the cornea, crystalline lens and other tissues of an eye, comprising:
   a laser source for producing a laser beam;
   a projector for projecting the laser beam onto an eye to be examined;
   scanning means for scanning the laser beam vertically and horizontally within a selected area of the eye to be examined to form thereon a slit image which illuminates the selected area;
   scanner controller means for varying scanning speed of the laser beam and varying the vertical and horizontal range of scanning;
   optical means for receiving light scattered by the selected area of the eye to be examined; and
   light regulating means for regulating the intensity of the laser beam to a predetermined level depending upon the quantity of light received by the optical means to obtain a substantially constant luminous intensity of the slit image irrespective of variations in the scanning image.

2. A slit lamp microscope as set forth in claim 1; wherein the light regulating means includes a pair of linear polarizers through which the laser beam passes, one of the linear polarizers being caused to rotate relative to the other polarizer to regulate the intensity of the laser beam depending upon the quantity of light received by the optical sensor.

3. A slit lamp microscope as set forth in claim 1; wherein the optical means includes means for photographing an image of the eye according to the received light.

4. An ophthalmologic microscope for observing the eye of a patient, comprising: laser means for producing a laser light beam; projecting means for projecting the laser light beam onto the eye of a patient; scanning means for scanning the laser light beam along a given locus within a designated area of the eye to form an illuminated slit pattern along the locus effective to illuminate the designated area of the eye, wherein the scanning means includes means for vertically and horizontally scanning the laser beam to form an illuminated slit pattern; scanner controller means for varying scanning speed of the laser beam and varying the vertical and horizontal range of scanning; and optical means receptive of light from the illuminated designated area of the eye for optically magnifying the light to form a magnified image of the designated area of the eye, wherein the optical means includes detecting means for detecting the quantity of the received light, and the laser means includes regulating means for regulating the intensity of the laser light beam according to the detected quantity of the light to obtain a substantially constant luminous intensity of the slit image irrespective of variations in the scanning range.

5. An ophthalmologic microscope according to claim 4; wherein the regulating means includes a pair of opposed linear polarizers disposed in the path of the laser light beam and being angularly displaceable relative to each other to regulate the laser light beam intensity.

6. An ophthamologic microscopic according to claim 4; wherein the optical means includes means for photographing the magnified image of the designated area of the eye.

7. An ophthalmologic microscope according to claim 4; including control means for designating an area of the eye to be observed to thereby enable the scanning means to scan the laser beam within the designated area of the eye.

* * * * *